US005801188A

United States Patent [19]

Hassenbusch, III et al.

[11] Patent Number: 5,801,188
[45] Date of Patent: Sep. 1, 1998

[54] CLONIDINE THERAPY ENHANCEMENT

[75] Inventors: Samuel J. Hassenbusch, III, Houston, Tex.; Patrick Edeburn, Maple Grove, Minn.; Lawrence A. Trissel, Houston, Tex.

[73] Assignee: Medtronic Inc., Minneapolis, Minn.

[21] Appl. No.: 781,030

[22] Filed: Jan. 8, 1997

[51] Int. Cl.$^6$ .............................................. A61K 31/415
[52] U.S. Cl. .................................................. 514/392
[58] Field of Search ........................................... 514/392

[56] References Cited

U.S. PATENT DOCUMENTS

| | | |
|---|---|---|
| 3,202,660 | 8/1965 | Zeile et al. |
| 4,122,190 | 10/1978 | Lancranjan ................... 514/392 |
| 4,692,147 | 9/1987 | Duggan ........................ 604/93 |
| 4,921,853 | 5/1990 | LeBlanc ...................... 514/227.2 |
| 5,459,133 | 10/1995 | Neufeld ....................... 514/215 |
| 5,523,316 | 6/1996 | Gan et al. .................... 514/392 |

OTHER PUBLICATIONS

Derwent Abstract No. 96–42061, Zakel et al., Acta anaesthesiol. Scand., 40, Suppl 109, p. 223, 1996.
Derwent Abstract No. 95–41208, Eisenach, et al. Anesthesiology 83, No. 1, pp. 33–47, 1995.
Roxane Laboratories, Inc., "DURACLON clonidine HCI Injection", Sep. 1996.
Roxane Laboratories, Inc., "Block another path of pain", Feb. 1997.
Quan et al., "Clonidine in Pain Management," Ann. of Pharmc., V27, pp. 313–314 (1993).
Eisenach et al., "Site of Hemodynamic Effects of Intrathecal $\alpha_2$-Adrenergic Agonists," Anesthesiology, V74, pp. 766–771 (1991).
Filos et al., "Intrathecal Clonidine as a Sole Analgesic for Pain Relief after Cesarean Section," Anesthesiology, V77, pp. 267–274 (1992).
Filos et al., "Hemodynamic and Analgesic Profile after Intrathecal Clonidine in Humans," Anesthesiology, V81, pp. 591–601, (1994).

Primary Examiner—Raymond Henley, III
Attorney, Agent, or Firm—Banner & Witcoff, Ltd.

[57] ABSTRACT

This invention provides methods for intraspinal administration of therapeutically-effective amounts of clonidine for alleviating acute and chronic pain.

31 Claims, 3 Drawing Sheets

FIG. 2

Blood Pressure Changes During Clonidine Infusion

| Clonidine Dose (micgm/hr) | Mean Systolic BP |
|---|---|
| 0 | 127.6 |
| 1 | 127.6 |
| 2 | 127.6 |
| 3 | 125.8 |
| 4 | 127.4 |
| 5 | 125.7 |
| 6 | 124.0 |
| 7 | 121.1 |
| 8 | 119.4 |
| 9 | 116.5 |
| 10 | 116.1 |
| 11 | 115.7 |
| 12 | 116.2 |
| 13 | 116.9 |
| 14 | 115.8 |
| 15 | 113.8 |
| 16 | 114.2 |
| 17 | 112.9 |
| 18 | 111.6 |
| 19 | 111.2 |
| 20 | 110.8 |
| 21 | 112.3 |
| 22 | 113.8 |
| 23 | 114.8 |
| 24 | 116.1 |
| 25 | 118.4 |
| 26 | 115.5 |
| 27 | 115.9 |
| 28 | 117.5 |
| 29 | 119.2 |
| 30 | 120.3 |
| 31 | 124.9 |
| 32 | 124.9 |
| 33 | 124.8 |
| 34 | 124.8 |
| 35 | 124.8 |
| 36 | 123.8 |
| 37 | 122.9 |
| 38 | 121.9 |
| 39 | 120.9 |
| 40 | 124.0 |
| 41 | 129.6 |
| 42 | 129.5 |
| 43 | 129.4 |
| 44 | 129.3 |
| 45 | 131.4 |
| 46 | 131.3 |
| 47 | 130.0 |
| 48 | 129.8 |
| 49 | 129.7 |

| Age | Sex | Diagnosis | End Dose | % Pain Relief | Success/ Failure |
|---|---|---|---|---|---|
| 41 | F | CNP | 576 | 75% | s |
| 68 | F | CNP | 744 | 80% | s |
| 65 | F | CNP | 744 | 80% | s |
| 55 | M | CNP | 840 | 70% | s |
| 63 | M | CNP | 960 | 90% | s |
| 32 | F | CNP | 1008 | 50% | s |
| 23 | F | CNP | 1056 | 75% | s |
| 65 | F | CNP | 1104 | 80% | s |
| 41 | F | CNP | 1104 | 80% | s |
| 46 | F | CNP | 1140 | 80% | s |
| 43 | M | Ca | 1200 | 90% | s |
| 38 | F | CNP | 1200 | 50% | s |
| MEAN for Success Patients | | | 973 | 75% | |

FIG. 3

CLONIDINE THERAPY ENHANCEMENT

BACKGROUND OF THE INVENTION

1. Field of the Invention

This invention relates to a method for intraspinal administration of an analgesically-effective amount of clonidine to a human without causing a clinically-adverse hemodynamic effect on the human.

2. Description of the Prior Art

Clonidine is an $\alpha_2$-adrenergic receptor agonist that has been primarily used as a systemic antihypertensive agent when administered orally or by intravenous injection. Clonidine has also been investigated for its effectiveness as an analgesic. Although recognized as having analgesic properties, use of the drug at analgesically-effective doses has been associated with a variety of deleterious hemodynamic side effects, principal among these being severe hypotension and bradycardia.

Eisenach and Tong, 1991, *Anesthesiology* 74: 766–771 reported that thoracic intrathecal administration of clonidine in sheep resulted in hypotension and bradycardia.

Filos et al., 1992, *Anesthesiology* 77: 267–274 reported that intrathecal clonidine administration at doses of 150 µg resulted in analgesia in women undergoing caesarean section, but was associated with hemodynamic side effects including hypotension even in clinical settings where hemodynamics are closely controlled.

Quan et al., 1993, *Annals Pharmacother.* 27: 313–316 reviewed the results of a number of clinical trials of clonidine as an analgesic, which studies typically reported adverse hemodynamic side effects of intrathecal clonidine administered in doses of 150–450 µg.

Filos et al., 1994, *Anesthesiology* 81: 591–601 reported that intrathecal clonidine administration in humans can be used at doses of 450 µg in post-operative settings, resulting in sedation and under conditions where the patients were managed to minimize hemodynamic side effects.

Eisenach et al., 1995, *Pain* 61:391–399 describes a clinical study using epidural administration of a combination of clonidine and morphine for analgesia.

The prior art thus taught use of intrathecal clonidine to provide analgesia in acute surgical settings and for relief of post-surgical pain. The art also recognized that intrathecal clonidine administration was limited to a maximum daily dose of 450 µ/day, even in such closely-managed clinical settings. However, the recognized hemodynamic side effects of clonidine administration have prevented the widespread use of intrathecal clonidine in patients who suffer chronic pain. Sufferers of such pain are currently treated with opiates such as morphine, which are associated with a multiplicity of negative side effects, including tolerance, toxicity, nausea and vomiting, sedation, pruritus and physical dependence. There was thus an unfulfilled need in the art to develop a treatment regime that would permit the use of intrathecally-administered clonidine in the treatment of chronic pain without the accompanying adverse hemodynamic side effects, so that clonidine could be used in place of, or in addition to, opiates in the management of chronic pain patients.

SUMMARY OF THE INVENTION

The present invention provides a method for intraspinal, most preferably intrathecal, administration of clonidine to a human patient suffering from acute or chronic pain, most preferably neuropathic pain, in the absence of clinically-adverse hemodynamic effects. The method of the invention provides for administration of an increasing dose of clonidine throughout a treatment regime, wherein the amount of clonidine administered intraspinally is gradually increased over the treatment period to minimize adverse hemodynamic side effects. In preferred embodiments, the drug is administered intrathecally or epidurally, most preferably intrathecally. The invention provides for intrathecal administration of up to about 1200 µ/day clonidine over a treatment period of about 4 to 12 weeks. The invention also provides for intrathecal clonidine administration whereby the amount of clonidine administered is increased periodically, preferably between once and about three-times per day. In preferred embodiments, intrathecal administration is controlled using an implantable, programmable drug administration system. Clonidine administration according to the method of the invention is increased by about 0.5 to about 5 µg/hr during the administration period, resulting in a clinically-effective dose of from 4 to 50 µg/hr. The method of the invention is useful for treating chronic pain, particularly neuropathic pain.

Also provided by the invention is a pharmaceutical composition of clonidine at high dose (i.e., 1000–1500 µg/mL) for administration using the methods of the invention.

Specific preferred embodiments of the present invention will become evident from the following more detailed description of certain preferred embodiments and the claims.

BRIEF DESCRIPTION OF THE DRAWINGS

FIG. 2 is a numeric representation of mean systolic blood pressure and intrathecal clonidine dose.

FIG. 3 summarizes the doses at which most patients experience maximum pain relief.

DETAILED DESCRIPTION OF PREFERRED EMBODIMENTS

Figure 1:
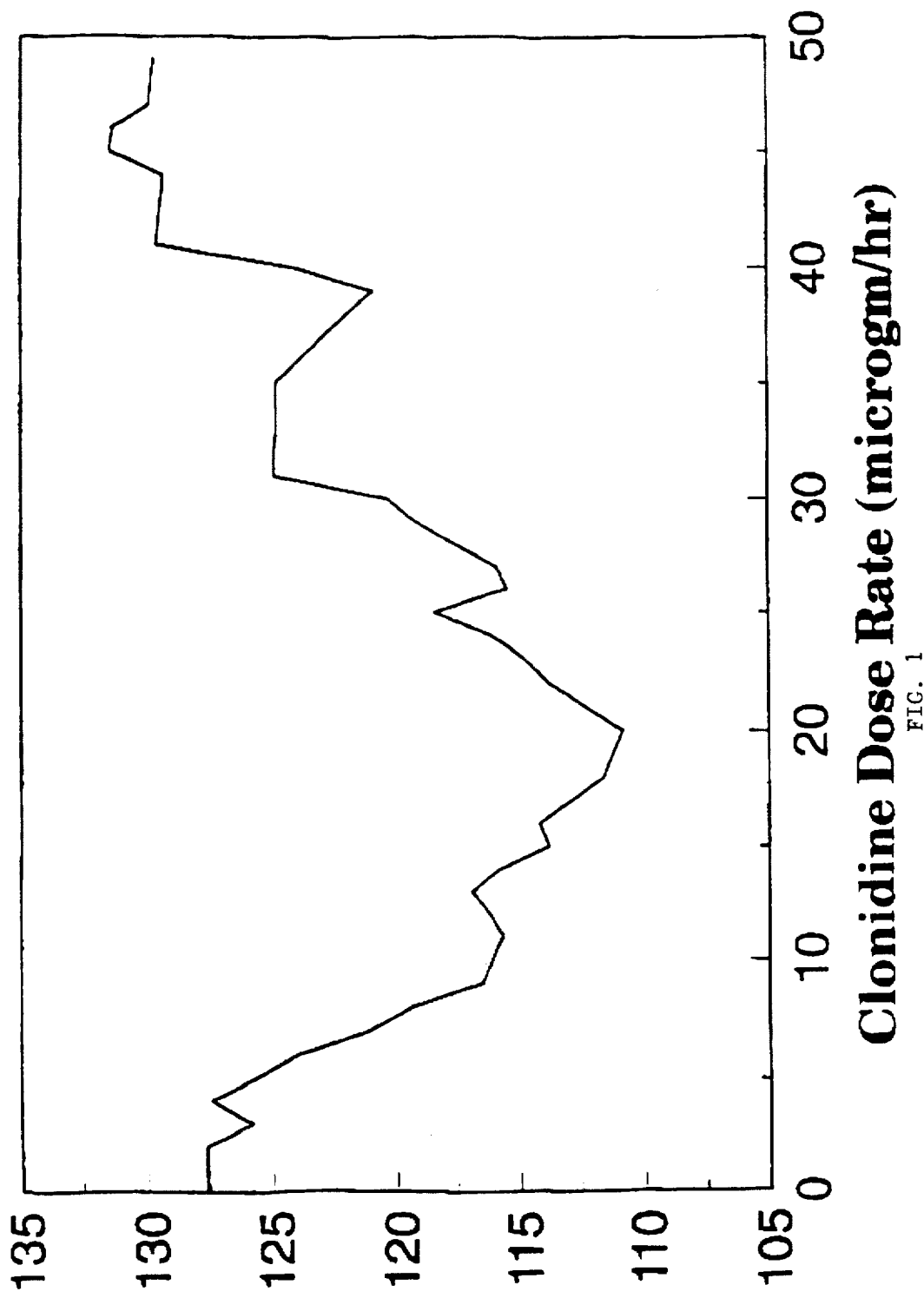
FIG. 1 is a graphical representation of the relationship between percent change in mean systolic blood pressure and clonidine administration dose over the course of a treatment period as disclosed herein, wherein the "watershed" dose is typically 20 µg/hr.

The present invention provides a method for intraspinal administration of clonidine to achieve an analgesic effect in human patients with acute or chronic pain while avoiding the adverse hemodynamic side effects which heretofore prevented intraspinal, specifically intrathecal, administration of clonidine at analgesically-effective doses. For the purposes of this invention, the term "intraspinal" will be understood to encompass both intrathecal and epidural administration sites and regimens.

The method of the invention is based in part on the discovery by the instant inventors that clonidine administration at gradually increasing doses over a treatment period of about 4 to 12 weeks permits administration of high levels of the drug (i.e., 900–1200 µg/day) with minimal adverse hemodynamic effects. It has unexpectedly been found that clonidine administration according to this increasing "slow-dose" protocol results in a patient undergoing a "watershed" or minimum hypotensive course, after which administration of increasing doses of clonidine is no longer associated with hypotension (see FIG. 1). Thus, careful management of clonidine administration by gradually increasing the administered dose over a treatment period has been found to result in significant clinical pain relief with minimal to no adverse hemodynamic side effects.

In preferred embodiments, the invention provides a clonidine administration method wherein the drug is administered over a 4 to 12 week administration period. It will be recognized that the length of the administration period is dependent on a patient's tolerance for the administered dose of clonidine, and that times both greater than and less than the 4-12 week "window" disclosed herein are useful for certain patients. The duration of the administration period is determined by the patient's tolerance for administered clonidine in the absence of adverse hemodynamic side effects or respiratory depression.

Over the course of treatment disclosed herein, the amount of administered clonidine is gradually increased from about 100 µg/day to up to about 1200 µg/day. The amount of clonidine administered is dependent on a patient's tolerance for the administered dose, and the extent of hemodynamic reaction and pain alleviation in each patient. Clonidine is administered in amounts sufficient to cause an increasing amount of pain relief without the concomitant induction of adverse hemodynamic side effects. In general, hemodynamic side effects are tolerated to the extent of about a 20% decrease in systolic pressure accompanying intrathecal clonidine administration, or wherein the mean arterial (systolic) pressure is not less than 80 mmHg.

For management of chronic pain, the preferred routes of administration are intrathecal and epidural. It will be understood in the art that the clonidine dose administered epidurally is generally about one-tenth of the dose administered intrathecally. Specifically, the dose can be administered intrathecally to the cervical spine, the thoracic spine, lumbar spine or the sacral spine.

Preferably, clonidine is administered continuously to a patient at a gradually-increasing dose. The dose administered is from about 4 to about 50 µg/hr. Typically, clonidine is administered intrathecally at about 1 to 4 µg/hr at the beginning of the treatment period, and at about 40 to 50 µg/hr at the end of the treatment period. The dose of clonidine administered intrathecally is increased gradually, for example, by about 0.2 to about 5 µg/hr wherein the administered dose is increased periodically from about one to three times per day.

In preferred embodiments, the dose of clonidine is administered intrathecally using an implantable drug administration system that is capable of being manually programmed by a physician to gradually increase the administered dose continuously or most preferably in discrete steps. Non-limiting examples of such an implantable drug administration system include devices as disclosed in U.S. Pat. No. 4,692,147 and, in a commercially-available embodiment, SynchroMed® Infusion System. Relevant features of such drug administration systems are ease of use, programmability, flexibility, sterility and reliability in delivering a gradually increasing clonidine dose over the course of a treatment period.

For the purposes of this invention, the term "adverse hemodynamic side effect" is intended to include but is not limited to hypotension and bradycardia, specifically wherein the systolic pressure is less than about 80 mmHg, and intolerable side effects, such as lightheadedness and/or dizziness.

For the purposes of this invention, "pain relief" and "analgesically-effective" and "therapeutically effective" are intended to mean greater than 50% pain relief to a patient, as determined using standard pain intensity instruments including but not limited to the Visual Analogue Scale of pain intensity and the Verbal Digital Scale of pain intensity (see Choiniere et al., 1990, Pain 40: 143-152 and Littman et al., 1985, Clin. Pharmacol. Ther. 16-23).

The method of this invention is useful in treating humans, as well as other animal species, suffering from acute or chronic pain. The method of the invention is particularly useful in the treatment of chronic pain in a human, because clonidine administration at clinical doses as disclosed herein is not associated with significant side effects of tolerance, toxicity, nausea and vomiting, sedation, pruritus and physical dependence that are associated with opiates, the only currently available treatment.

The method of this invention is useful for treating chronic pain, particularly neuropathic pain. Non-limiting examples of diseases and disorders in humans associated with the types of pain advantageously treated using the methods of this invention include spinal cord injury, plexopathy, diabetic neuropathy, post-herpetic neuralgia, phantom limb pain, stump pain in amputees, peripheral neuropathy, peripheral nerve injury, AIDS neuropathy, reflex sympathetic dystrophy, and pain associated with primary and metastatic neoplasia.

In addition to the above advantages of intrathecal clonidine administration described herein, the methods of this invention have the advantage of analgesic relief of pain in the absence of respiratory depression which is commonly associated with conventional alternative analgesic agents.

The invention also provides a pharmaceutical composition of clonidine for administration using the methods of the invention. Such pharmaceutical compositions are characterized whereby the composition comprises a concentration of clonidine at 1000-1500 µg/mL. Pharmaceutical compositions of the invention also comprise pharmaceutically-acceptable carriers, buffers, diluents and excipients.

The methods of this invention are more fully illustrated in the following Example. This Example illustrates certain aspects of the above-described method and advantageous results, and are shown by way of illustration and not limitation.

EXAMPLE 1

Clinical Study

A clinical study of the effectiveness on pain management using the clonidine administration method of the invention was performed. Twenty-seven patients suffering from chronic pain due to various etiologies were enrolled in the study. Details of the course of clonidine treatment, symptoms and side effects are shown in Table I. In sum, 12 of the 27 patients (44%) reported pain relief, with an average effectiveness of 75.7%, as reported by the patients using either the Visual Analogue Scale and/or Verbal Digital Scale of pain relief. Relief was positively associated with dose, with the mean effective dose of about 973 µg/day. The significance of these results is that the inventive method permitted administration of these high doses of clonidine without the hemodynamic side effects previously associated with 3- to 10-fold lower clonidine dosages. These results were particularly significant because this group of patients had failed all other attempted alternative treatment modalities, including intraspinal opiate administration. No new or heretofore unreported side effects of intrathecal clonidine treatment were reported, even though these doses were 3-10 fold higher than doses known prior to the instant invention. These results are shown graphically in FIG. 2.

It should be understood that the foregoing disclosure emphasizes certain specific embodiments of the invention and that all modifications or alternatives equivalent thereto are within the spirit and scope of the invention as set forth in the appended claims.

TABLE I

| # | Age | Sex | Diag.[a] | Dose/d | Durat'n | VDS[b] | Sympt.[c] | % relief | SideFX[d] | Rating[e] |
|---|-----|-----|----------|--------|---------|--------|-----------|----------|-----------|-----------|
| 1 | 44 | M | Ca | 1200 μg | 5.3 | 6–8 | A, C | 26 | RHBP | F |
| 2 | 28 | F | RSD | 1200 | 4.5 | 10 | A, B | 30% | ↓BP/wt | F |
| 3 | 45 | M | Ca | 24 | 0.25 | NA | NA | NA | NA | NA |
| 4 | 43 | M | Ca | 1200 | 9.5 | 2 | None | 90% | ↓BP | S |
| 5 | 77 | M | RSD | 720 | 1 | 9 | None | 10% | BP, HA | F |
| 6 | 63 | M | RSD | 960 | 13.8 | 2 | A | 90% | Edema | S |
| 7 | 29 | F | RSD | 1200 | 6.3 | 7 | A | 10% | BP, HA | F |
| 8 | 53 | F | RSD | 900 | 5 | 8 | A | 10% | BP, CD | F |
| 9 | 28 | M | RSD | 144 | 1.5 | 9 | None | 0% | HA | F |
| 10 | 32 | F | RSD | 1008 | 12.1 | 4 | None | 50% | N/HA | S |
| 11 | 55 | M | RSD | 840 | 2 | 4 | None | 70% | MC | S |
| 12 | 37 | F | RSD | 552 | 5.3 | 7 | A | 10% | ↓BP, ↓P | F |
| 13 | 43 | F | RSD | 600 | 3 | 7.5 | None | 10% | ↓BP, ↓P | F |
| 14 | 23 | F | RSD | 1056 | 11.2 | 4 | None | 75% | RHBP | S |
| 15 | 43 | F | RSD | 240 | 4 | 9 | None | 0% | D/Lth | F |
| 16 | 44 | M | RSD | 192 | 0.8 | 7 | None | 5% | None | F |
| 17 | 68 | F | FM | 744 | 10.2 | 4 | None | 80% | BP | S |
| 18 | 65 | F | FN | 744 μg | 10.2 | 2–3 | None | 80% | ↓BP | S |
| 19 | 38 | F | RSD | 1200 | 10.2 | 4–5 | None | 50% | None | S |
| 20 | 65 | F | RSD | 1104 | 7.2 | 7 | None | 80% | RN/V | S |
| 21 | 54 | M | RSD | 1200 | 3.1 | 7 | None | 20% | L/IMP | F |
| 22 | 37 | F | RSD | 624 | 1.5 | 9 | None | 0% | BP | F |
| 23 | 41 | F | RSD | 1104 | 6.5 | 3–4 | None | 80% | None | S |
| 24 | 41 | F | RSD | 576 | 6.1 | 3 | ID | 75% | Const. | S |
| 25 | 74 | F | Arach. | 960 | 2 | 4–5 | None | 50% | Leth. | F |
| 26 | 61 | F | RSD | 912 | 4.5 | 10 | None | 0% | Leth. | F |
| 27 | 46 | F | RSD | 1140 | 3.8 | 2 | None | 80% | None | S |
| 28 | 43 | M | Arach. | 1200 | 2 | 7.5 | None | 10% | P/BV | F |
| 29 | 44 | M | RSD | 588 | 1 | 6 | None | 15% | BP | NA |

[a]Diagnoses include carcinoma (Ca), reflex systemic dystrophy (RSD), arachnoiditis (Arach.), and femoral neuropathy (FN)
[b]VDS is Visual Digital Scale
[c]Other symptoms include decreased allodynia (A), decreased vasomotor effects (B), and decreased sweat production (C).
[d]Side effects include rebound high blood pressure (RHBP), decreased blood pressure (hypotension; ↓BP), corneal dystrophy (CD), mental confusion (MC), weight gain (↑ wt), headache (HA), leg edema (edema), constipation (const.), nausea/vomiting (N/V), lethargy (leth.) and impotence (imp.).
[e]Ratings include treatment success (S) or failure (F)
NA = not available

We claim:

1. A method for achieving an analgesic effect in a human, the method comprising intraspinal administration to the human of an increasing and analgesically-effective dose of clonidine over a treatment period whereby administration is unaccompanied by clinically-adverse hemodynamic effects.

2. The method of claim 1, wherein the clinically-adverse hemodynamic effect is hypotension.

3. The method of claim 1, wherein the clinically-adverse effect is bradycardia.

4. The method of claim 1, wherein clonidine is administered intrathecally.

5. The method of claim 1, wherein clonidine is administered epidurally.

6. The method of claim 1 wherein clonidine is administered intrathecally to the cervical spine, the thoracic spine, the lumbar spine or the sacral spine.

7. The method of claim 1, wherein clonidine is administered intrathecally using an implantable, programmable drug administration system or device.

8. The method of claim 1, wherein clonidine is administered over a treatment period of from about 4 to about 12 weeks.

9. The method of claim 1, wherein clonidine is continuously administered.

10. The method of claim 1, wherein clonidine is administered at a dose of from about 4 to about 50 μg/hr during at least a portion of the treatment period.

11. The method of claim 1, wherein clonidine is administered at about 1 to about 4 μg/hr at the beginning of the treatment period.

12. The method of claim 1, wherein clonidine is administered at about 40 to 50 μg/hr at the end of the treatment period.

13. The method of claim 1, wherein the dose of clonidine administered is increased by about 0.2 to about 5 μg/hr.

14. The method of claim 1, wherein the dose of clonidine administered is increased from once to about three times per day.

15. The method of claim 1 wherein the dose of clonidine administered is from about 450 to about 1200 μg/day.

16. The method of claim 1, wherein the dose of clonidine administered is therapeutically-effective in alleviating chronic neuropathic pain in the human.

17. The method of claim 1, wherein the dose of clonidine administered is therapeutically-effective in alleviating chronic neuropathic pain in the human associated with spinal cord injury, plexopathy, diabetic neuropathy, postherpetic neuralgia, phantom limb pain, stump pain in amputees, peripheral neuropathy, peripheral nerve injury, AIDS neuropathy, reflex sympathetic dystrophy, or primary or metastatic neoplasia.

18. The method of claim 1, wherein said dose of clonidine is administered at a concentration in excess of 500 μg/mL.

19. The method of claim 1, wherein said dose of clonidine is administered at a concentration of about 500 to 4000 μg/mL.

20. The method of claim 1, wherein said dose of clonidine is administered at a concentration of about 1000 to about 2000 µg/mL.

21. A method for achieving an analgesic effect in a human having a heart beat, the method comprising the steps of:

monitoring the heart beat in the human; and administering intraspinally to the human an increasing and analgesically-effective dose of clonidine over a treatment period in a dose responsive to the step of monitoring the heart beat to minimize or eliminate bradycardia.

22. A method for achieving an analgesic effect in a human body, the method comprising the steps of:

implanting in the body, a reservoir of clonidine and a delivery system for the clonidine, the delivery system connected to the reservoir; and administering intraspinally to the human body, from the reservoir and through the delivery system, an increasing and analgesically-effective dose of clonidine over a treatment period.

23. A method for achieving an analgesic effect in a human body, the method comprising the steps of:

implanting in the body, a reservoir of clonidine and a delivery system for the clonidine, the delivery system connected to the reservoir; and administering intraspinally to the human body, from the reservoir and through the delivery system, an increasing and analgesically-effective dose of clonidine over a treatment period, whereby administration is unaccompanied by adverse hemodynamic or pulmonary effects.

24. A method for achieving an analgesic effect in a human, the method comprising the steps of:

monitoring hemodynamic effects in the human; and administering intraspinally to the human an increasing and analgesically-effective dose of clonidine over a treatment period, said dose responsive to the step of monitoring hemodynamic effects to minimize or eliminate hemodynamic effects, whereby administration is unaccompanied by adverse hemodynamic effects.

25. The method of claims 21, 22, 23 or 24 wherein the clonidine is administered intrathecally.

26. The method of claims 21, 22, 23 or 24 wherein the clonidine is administered over a treatment period of from about 4 to about 12 weeks.

27. The method of claims 21, 22, 23 or 24 wherein the clonidine is continuously administered.

28. The method of claims 21, 22, 23 or 24 wherein the dose of clonidine administered is therapeutically-effective in alleviating chronic neuropathic pain in the human.

29. The method of claims 21, 22, 23 or 24 wherein said dose of clonidine is administered at a concentration in excess of 500 µg/mL.

30. The method of claims 21, 22, 23 or 24 wherein said dose of clonidine is administered at a concentration of about 500 to 4000 µg/mL.

31. The method of claims 21, 22, 23 or 24 wherein said dose of clonidine is administered at a concentration of about 1000 to about 2000 µg/mL.

* * * * *